US008788062B2

(12) United States Patent
Clark et al.

(10) Patent No.: US 8,788,062 B2
(45) Date of Patent: Jul. 22, 2014

(54) POLYMER COMPRESSION JOINING IN IMPLANTABLE LEAD

(75) Inventors: Bryan A. Clark, Coon Rapids, MN (US); Benjamin J. Haasl, Forest Lake, MN (US); Brian L. Schmidt, White Bear Lake, MN (US); Arthur J. Foster, Centerville, MN (US); Daniel J. Foster, Lino Lakes, MN (US); Duane T. Meyer, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 332 days.

(21) Appl. No.: 12/832,618

(22) Filed: Jul. 8, 2010

(65) Prior Publication Data

US 2011/0034980 A1    Feb. 10, 2011

Related U.S. Application Data

(60) Provisional application No. 61/231,170, filed on Aug. 4, 2009.

(51) Int. Cl.
*A61N 1/05* (2006.01)
*A61N 1/375* (2006.01)

(52) U.S. Cl.
CPC ............ *A61N 1/05* (2013.01); *A61N 1/3752* (2013.01)
USPC .......................... 607/116; 600/373; 600/374

(58) Field of Classification Search
CPC ............................ A61N 1/05; A61N 1/3752
USPC .......... 607/116–119, 122, 123; 600/373, 374
See application file for complete search history.

(56) References Cited

U.S. PATENT DOCUMENTS

| 4,328,812 | A | | 5/1982 | Ufford et al. |
| 4,506,680 | A | * | 3/1985 | Stokes ........................ 607/120 |
| 4,589,418 | A | | 5/1986 | Gopikanth |
| 5,385,578 | A | * | 1/1995 | Bush et al. .................. 607/122 |
| 5,480,416 | A | | 1/1996 | Garcia et al. |
| 5,488,768 | A | * | 2/1996 | Mar .............................. 29/860 |
| 5,683,443 | A | | 11/1997 | Munshi et al. |
| 5,921,933 | A | | 7/1999 | Sarkis et al. |
| 5,968,086 | A | * | 10/1999 | Bonner et al. ............... 607/122 |
| 6,047,217 | A | | 4/2000 | Uhrberg |
| 6,148,237 | A | * | 11/2000 | Das ............................. 607/122 |
| 6,295,474 | B1 | | 9/2001 | Munshi |
| 6,304,786 | B1 | | 10/2001 | Heil, Jr. et al. |
| 6,505,081 | B1 | | 1/2003 | Das |
| 6,506,457 | B2 | | 1/2003 | Hum |
| 6,584,363 | B2 | | 6/2003 | Heil, Jr. et al. |
| 6,611,720 | B2 | | 8/2003 | Hata et al. |
| 6,692,834 | B1 | | 2/2004 | Martinez et al. |
| 6,718,628 | B2 | | 4/2004 | Munshi |

(Continued)

*Primary Examiner* — Niketa Patel
*Assistant Examiner* — Christopher A Flory
(74) *Attorney, Agent, or Firm* — Faegre Baker Daniels LLP

(57) ABSTRACT

Implantable medical leads and methods of forming such leads are disclosed. An implantable medical lead includes a lead body, a swage base coupled to the lead body, and a polymeric member interposed at least in part between the swage base and at least one rigid component of the lead such as an electrode or annular ring. The swage base includes an annular-shaped body including a flange having a number of protrusions that extend radially outward from the flange. During a swaging process, the protrusions on the flange are compressed against the polymeric member, forming a number of channels in the member that mechanically bond the member to the swage base.

20 Claims, 8 Drawing Sheets

(56) References Cited

U.S. PATENT DOCUMENTS

| | | |
|---|---|---|
| 6,830,583 B2 | 12/2004 | Shah et al. |
| 6,844,023 B2 | 1/2005 | Schulman et al. |
| 6,949,095 B2 | 9/2005 | Vaska et al. |
| 7,001,421 B2 | 2/2006 | Cheng et al. |
| 7,105,198 B2 | 9/2006 | Sundar |
| 7,218,971 B2 | 5/2007 | Heil, Jr. et al. |
| 7,221,982 B2 | 5/2007 | Aron et al. |
| 7,225,024 B2 | 5/2007 | Zhu et al. |
| 7,279,112 B2 | 10/2007 | Martinez |
| 7,282,213 B2 | 10/2007 | Schroeder et al. |
| 7,352,560 B2 | 4/2008 | Poplett et al. |
| 7,410,509 B2 | 8/2008 | Eberhard et al. |
| 7,546,165 B2 | 6/2009 | Zarembo et al. |
| 2001/0044646 A1* | 11/2001 | Marshall et al. ............ 607/127 |
| 2005/0131509 A1 | 6/2005 | Atanassoska et al. |
| 2006/0008500 A1 | 1/2006 | Chavan et al. |
| 2006/0035026 A1 | 2/2006 | Atanassoska et al. |
| 2006/0240059 A1 | 10/2006 | Bavaro et al. |
| 2006/0240253 A1 | 10/2006 | Bavaro et al. |
| 2007/0051531 A1 | 3/2007 | Borgaonkar et al. |
| 2007/0184197 A1 | 8/2007 | Aron et al. |
| 2007/0191921 A1 | 8/2007 | Zhu et al. |
| 2007/0239245 A1 | 10/2007 | Borgaonkar et al. |
| 2007/0255378 A1 | 11/2007 | Polkinghorne et al. |
| 2007/0299491 A1 | 12/2007 | Borgaonkar et al. |
| 2008/0132984 A1 | 6/2008 | Schell |
| 2008/0155800 A1 | 7/2008 | Poplett et al. |
| 2009/0048652 A1 | 2/2009 | Malik et al. |
| 2009/0054961 A1 | 2/2009 | Borgaonkar et al. |
| 2009/0076576 A1 | 3/2009 | Hall et al. |
| 2009/0192577 A1 | 7/2009 | Desai |
| 2009/0192580 A1 | 7/2009 | Desai |
| 2010/0241204 A1 | 9/2010 | Scheuermann |

* cited by examiner

POLYMER COMPRESSION JOINING IN IMPLANTABLE LEAD

CROSS-REFERENCE TO RELATED APPLICATIONS

This application claims the benefit under 35 U.S.C. §119 of U.S. Provisional Application No. 61/231,170, filed Aug. 4, 2009, entitled "Polymer Compression Joining in Implantable Leads," which is incorporated herein by reference in its entirety for all purposes.

TECHNICAL FIELD

The present invention relates generally to implantable medical devices. More specifically, the present invention pertains to implantable medical electrical leads and to methods of forming such leads.

BACKGROUND

Various types of implantable medical electrical leads for use in cardiac rhythm management and neurostimulation are known. In cardiac rhythm management applications, for example, pacemaker or defibrillator leads are sometimes used to provide an electrical stimulus to a patient's heart and/or to sense cardiac electrical activity occurring within the body. Such leads are typically advanced intravascularly to an implantation location on or within the patient's heart, and are coupled to a pulse generator or other implantable device for delivering electrical stimulus energy to the leads. The leads are typically constructed to have a minimal profile to facilitate insertion of the lead through the body during implantation, and are often flexible to accommodate natural patient movement of the lead at the implantation site.

Implantable medical electrical leads used in cardiac and neurological applications often include an elongate, tubular sleeve that serves to electrically insulate the interior components of the lead from the surrounding body tissue and blood, and which provides additional mechanical strength to the lead. In some lead designs, a portion of the sleeve may be connected proximally to a terminal connector that connects the proximal end of the lead to the pulse generator. Portions of the sleeve may also be connected to a number of electrodes on the lead that deliver electrical stimulus energy to adjacent body tissue.

The attachment of the sleeve to the terminal connector is typically accomplished by application of various biocompatible adhesives to the connector and the sleeve, in some cases in conjunction with a crimping process. The attachment of the sleeve to the electrodes, in turn, is typically accomplished using an adhesive alone and without crimping in order to maintain the desired flexibility of the lead. In use, the adhesive joints that connect the sleeve to the terminal connector and electrodes must offer adequate strength and sealing properties over the operational life of the lead.

SUMMARY

The present invention pertains to implantable medical electrical leads, and to methods of forming compressive joints on implantable medical electrical leads.

In Example 1, an implantable medical lead, comprising a lead body; a swage base coupled to the lead body, the swage base comprising an annular body including at least one flange and a number of protrusions extending radially outward from the at least one flange; a polymeric member interposed at least in part between the swage base and a rigid member; and wherein the polymeric member is mechanically bonded to the swage base and the rigid member via a compression joint. During a swaging or crimping process, the protrusions on the flange are compressed against the polymeric member, forming a number of channels in the member that mechanically bond the member to the swage base.

In Example 2, the implantable medical lead according to Example 1, wherein the rigid member includes an electrode.

In Example 3, the implantable medical lead according to Example 2, wherein the electrode is a ring electrode.

In Example 4, the implantable medical lead according to any of Examples 1-3, wherein the lead further includes a terminal connector, and wherein the electrode is a terminal electrode.

In Example 5, the implantable medical lead according to any of Examples 2-4, wherein the swage base comprises an electrically conductive material.

In Example 6, the implantable medical lead according to any of Examples 2-5, wherein the swage base electrically connects the electrode to a coil conductor.

In Example 7, the implantable medical lead according to Example 1, wherein the rigid member comprises an annular ring.

In Example 8, the implantable medical lead according to any of Examples 1-7, wherein each of the protrusions extend radially outward about a circumference of the annular body.

In Example 9, the implantable medical lead according to any of Examples 1-8, wherein the at least one flange comprises a first flange and a second flange, the first and second flanges each including a plurality of protrusions configured to engage an end of the polymeric member.

In Example 10, the implantable medical lead according to any of Examples 1-9, wherein the swage base further includes a locking tab.

In Example 11, the implantable medical lead according to any of Examples 1-10, wherein the polymeric member comprises an insulating sleeve.

In Example 12, an implantable medical lead, comprising: a coil conductor electrically coupled to an electrode; a metal swage base coupled to the coil conductor and electrode, the swage base comprising an annular body including at least one flange and a plurality of bumps extending radially outward from the at least one flange; a polymer sleeve interposed at least in part between the swage base and the electrode, the polymer sleeve including a number of channels each in compression with a corresponding bump of the swage base; and wherein the polymer sleeve is mechanically bonded to the swage base and the electrode via a compression joint.

In Example 13, the implantable medical lead according to Example 12, wherein the electrode is a ring electrode.

In Example 14, the implantable medical lead according to Example 12, wherein the lead further includes a terminal connector, and wherein the electrode is a terminal electrode.

In Example 15, the implantable medical lead according to any of Examples 12-14, wherein each of the bumps extend radially outward about a circumference of the annular body.

In Example 16, the implantable medical lead according to any of Examples 12-15, wherein the at least one flange comprises a proximal flange including a plurality of bumps configured to engage an end of a first polymeric sleeve, and a distal flange including a plurality of bumps configured to engage an end of a second polymeric sleeve.

In Example 17, a method of forming a joint on an implantable medical lead, the method comprising: coupling at least a portion of a polymeric member to a base, the base comprising an annular body including a flange with a number of protrusions configured to engage an inner wall of the polymeric member; inserting a rigid member over the polymeric member adjacent to the flange; and compressing the polymeric member in between the base and the rigid member, thereby forming a compression joint between the polymeric member, the base, and the rigid member.

In Example 18, the method according to Example 17, wherein compressing the polymeric member in between the base and the rigid member includes inserting a mandrel into an interior portion of the lead and applying a radial compressive force about the rigid member.

In Example 19, the method according to any of Examples 17-18, further comprising annealing the compression joint.

In Example 20, the method according to Example 19, wherein the polymeric member comprises a thermoplastic material, and wherein annealing the compression joint causes reflow of the polymeric member within a cavity between the base and rigid member.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
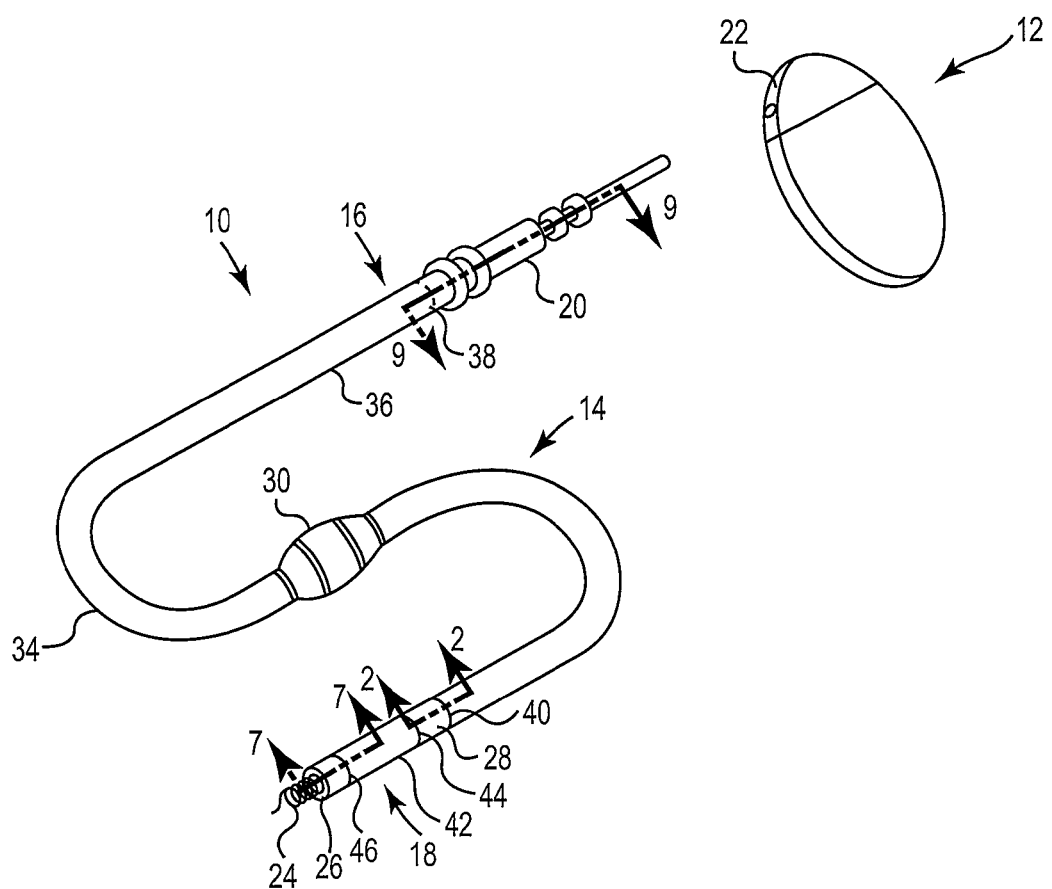
FIG. 1 is a perspective view of an implantable medical electrical lead and pulse generator in accordance with an illustrative embodiment.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a perspective view of an implantable medical electrical lead 10 and pulse generator 12 in accordance with an illustrative embodiment. The lead 10, illustratively a cardiac pacing lead, includes a lead body 14 having a proximal section 16 and a distal section 18. The proximal section 16 of the lead body 14 is coupled to a terminal connector 20 which, during the implantation procedure, is connected to a header 22 on the pulse generator 12. The pulse generator 12 may be pacemaker, a cardioverter defibrillator, or other type of implantable stimulator or sensing instrument. In the embodiment of FIG. 1, the lead 10 is a bipolar lead including a helical tip electrode 24 configured to retract out from within the distal end 26 of the lead 10, and one or more ring electrodes 28 located on the distal section 18 of the lead body 14, which function as an anode. Although FIG. 1 shows an example lead 10 having a bipolar electrode configuration, in other embodiments the lead 10 is a unipolar lead equipped with only a single electrode. Other bipolar, multipolar, or unipolar lead configurations are also possible.

The lead 10 can include a number of components to facilitate attachment of the lead 10 within the patient's body. In the embodiment of FIG. 1, for example, a suture sleeve 30 disposed over the proximal section 16 of the lead body 14 can be used during implantation to secure the lead 10 to body tissue at the site of transvenous entry into the vasculature. In those leads configured for transvenous entry via a blood vessel in the patient's chest region, for example, the suture sleeve 30 can be used to secure the lead 10 in or near the pocket below the patient's collarbone normally used to implant the pulse generator 12. During implantation, the rotation of the helical tip electrode 24 also serves to secure the distal end 26 of the lead 10 to the patient's heart.

During operation, the pulse generator 12 is configured to supply electrical energy to the electrodes 24,28 to provide electrical stimulus therapy to the patient's heart and/or to sense cardiac electrical activity occurring within the body. In cardiac pacing applications, for example, the lead 10 can be implanted on or within the patient's heart to treat an arrhythmia or other cardiac condition. In other applications, the lead 10 can be used to provide other desired therapies and/or to sense other parameters within the body. In one embodiment, for example, the lead 10 comprises a neurostimulator lead that can be used to deliver electrical impulses to the brain or spinal chord for treating chronic pain, tremors, or other neurological conditions.

An insulating sleeve 34 disposed over all or a substantial portion of the length of the lead body 14 is configured to electrically insulate the interior of the lead 10 from the surrounding body tissue and blood, and to provide additional mechanical strength to the lead 10. A first section 36 of the insulating sleeve 34 is coupled proximally to the lead body 14 at a first joint 38 located at or near the terminal connector 20, and distally at a second joint 40 located at or near the ring electrode 28. A second section 42 of the insulating sleeve 34, in turn, is coupled proximally at a third joint 44 at or near the ring electrode 28, and distally at a fourth joint 46 at or near the distal end 26 of the lead 10. The number and location of the joints 38,40,44 connecting the insulating sleeve 34 to the lead 10 will typically vary depending on the particular configuration of the lead 10.

The insulating sleeve 34 comprises a flexible tubular member that electrically insulates the interior components of the lead 10 from the surrounding body tissue and blood. The insulating sleeve 34 comprises a biocompatible, electrically non-conductive material such as silicone, polyurethane, silicone-polyurethane copolymer(s), polyetheretherketone, or the like. In some embodiments, the insulating sleeve 34 comprises a thermoplastic material (e.g., polyurethane) that permits reflow of the sleeve material during an annealing or thermoforming step used in fabricating the lead 10, as discussed further herein with respect to FIG. 4D.

Figure 2:
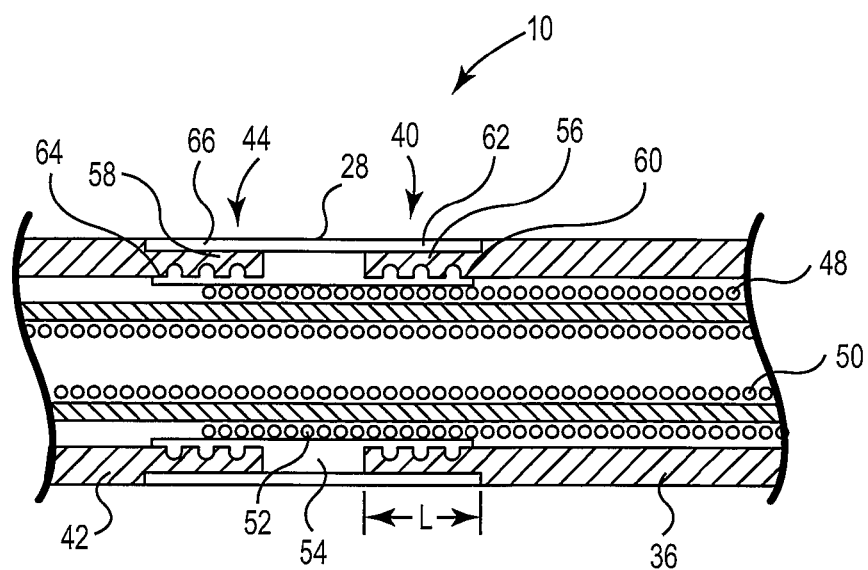
FIG. 2 is a longitudinal cross-sectional view along line 2-2 in FIG. 1 showing the connection of the insulating sleeve to the ring electrode.

FIG. 2 is a longitudinal cross-sectional view along line 2-2 in FIG. 1 showing the connection of the insulating sleeve 34 to the ring electrode 28. As further shown in FIG. 2, the insulating sleeve 34 connects to the ring electrode 28 at joints 40,44, forming a seal that prevents body tissue and blood surrounding the lead 10 from contacting the interior components of the lead 10, including a number of coil conductors 48,50 that transmit electrical energy through the lead 10 to each of the electrodes 24,28. A first coil conductor 48 is secured at a distal section 52 to an anode swage base 54, which in some embodiments, comprises an electrically conductive material that allows current from the ring electrode 28 to be transmitted through the base 54 to the coil conductor 48. In some embodiments, for example, the swage base 54 is formed from an electrically conductive metal such as 316 stainless steel, platinum, MP35N, or gold. A second coil conductor 50 extending through the interior of the lead 10, in turn, is electrically coupled to the tip electrode 24, and is used to supply current to the tip electrode 24 during stimulus therapy.

The ends 56,58 of the insulating sleeve 34 are each secured to a portion of swage base 54 and the ring electrode 28, forming a mechanical bond between the sleeve 34 and the swage base 54 and electrode 28 at each joint 40,44. A distal end 56 of the first insulating sleeve section 36 is coupled between a proximal flange 60 of the swage base 54 and a proximal section 62 of the ring electrode 28. A proximal end 58 of the second insulating sleeve section 42, in turn, is coupled between a distal flange 64 of the swage base 54 and a distal section 66 of the ring electrode 28. In some embodiments, and as further shown in FIG. 2, the ends 56,58 of the insulating sleeve 34 may have a reduced outer diameter such that the profile of the lead 10 is relatively constant at each of the joints 40,44. The reduced outer diameter can be imparted to the insulating sleeve 34, for example, during the swaging and annealing process used to mechanically bond the insulating sleeve 34 to the swage base 54 and ring electrode 28, as discussed further herein.

The engagement length L at which the ends 56,58 of the insulating sleeve 34 are engaged to the swage base 54 and ring electrode 28 may vary depending on the thickness of the sleeve 34, the type of material use to form the sleeve 34, the desired mechanical characteristics of the bond between the sleeve 34 and the swage base 54 and ring electrode 28, as well as other factors. In some embodiments, for example, the engagement length L may be a minimum of about 4 times the thickness of the insulating sleeve 34 prior to swaging. In other embodiments, the engagement length L may be greater or less than 4 times the thickness of the insulating sleeve 34 prior to swaging.

Figure 3:
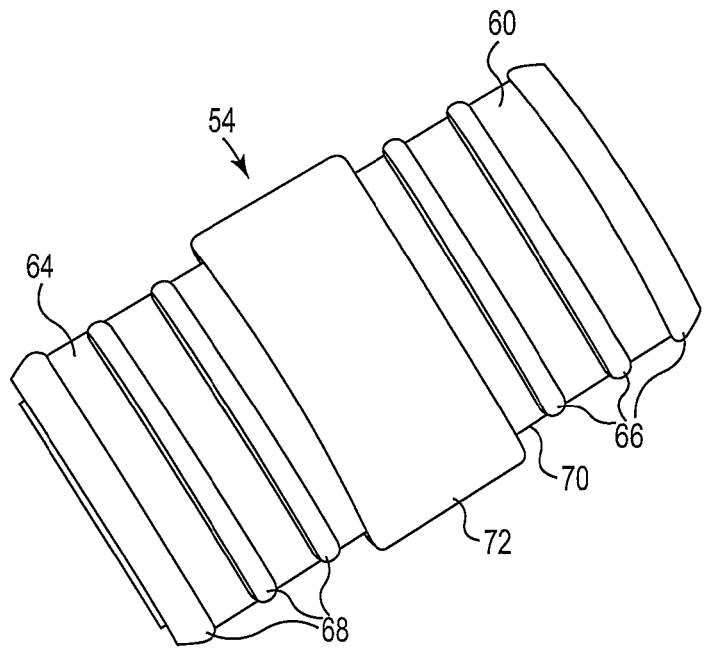
FIG. 3 is a perspective view showing the swage base of FIG. 2 in greater detail.

FIG. 3 is a perspective view showing the swage base 54 of FIG. 2 in greater detail. As can be further seen in FIG. 3, the proximal and distal flanges 60,64 each include a number of protrusions 66,68 that extend radially outward about the circumference of an annular body 70. In certain embodiments, for example, each of the flanges 60,64 include three protrusions 66,68 configured to engage the ends 56,58 of the insulating sleeve 34 during swaging to form a mechanical bond between the sleeve 34 and the swage base 54 and ring electrode 28. In other embodiments, each of the flanges 60,64 can include a greater or lesser number of protrusions 66,68. A relatively large diameter portion 72 of the annular body 70 is configured to contact a portion of the ring electrode 28, providing an electrical pathway between the first coil conductor 48 and the electrode 28. During the swaging process, the protrusions 66,68 serve to further bond the ends 56,58 of the insulating sleeve 34 to the swage base 54 by imparting localized, compressive stresses to the interior wall of the sleeve 34.

The height of each of the protrusions 66,68 may be sufficient to cause a reduction of thickness of the insulating sleeve 34 at the location where the protrusions 66,68 contact the inner wall of the sleeve 34. In some embodiments, for example, the height of each of the protrusions 66,68 may be approximately 10% to 50% of the overall thickness of the insulating sleeve 34 subsequent to swaging. In the embodiment shown, the protrusions 66,68 comprise a number of semi-circular bumps which, when compressed against the ends 56,58 of the insulating sleeve 34, impart several semi-circular channels within the sleeve material. The configuration of the protrusions 66,68 may vary, however. In some embodiments, for example, the protrusions 66,68 may comprise V-shaped bumps. In another embodiment, the protrusions 66,68 may comprise threads that extend helically about the body 70 at each of the flanges 60,64.

FIGS. 4A-4D are several views showing an illustrative method of coupling a polymer sleeve to a lead. FIGS. 4A-4D may represent, for example, several illustrative steps used to mechanically bond the insulating sleeve 34 to the ring electrode 28 of FIG. 1. The steps discussed herein can also be used to mechanically bond the insulating sleeve 34 to other components of the lead 10, including the tip electrode 24 and the terminal connector 20.

Figure 4A:
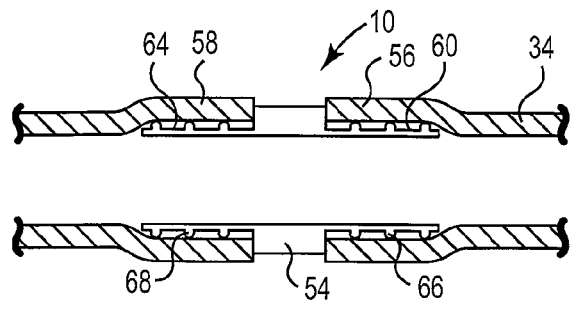
FIGS. 4A-4D are several views showing an illustrative method of coupling an insulating sleeve to a lead.

In a first step depicted in FIG. 4A, the ends 56,58 of the insulating sleeve 34 are advanced over the proximal and distal flanges 60,64 of the swage base 54. In some embodiments, and as shown in FIG. 4A, the inner diameter of each of the sleeve ends 56,58 is slightly smaller than the outer profile of the swage base 54 at each of the flanges 60,64, causing the ends 56,58 of the sleeve 34 to radially stretch when engaged over the protrusions 66,68. This stretching creates a friction fit which serves to hold the sleeve ends 56,58 secure against the swage base 54 during later processing steps.

Figure 4B:
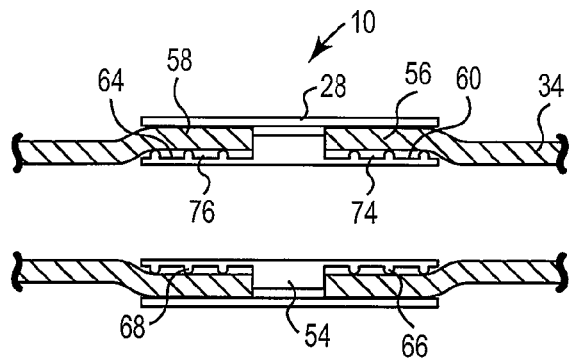

Once the insulating sleeve 34 is secured to the flanges 60,64, and as further shown in another view in FIG. 4B, the ring electrode 28 is then advanced over the assembly and aligned adjacent to the swage base 54, thus sandwiching the ends 56,58 of the sleeve 34 within respective spaces or cavities 74,76 located between the swage base 54 and ring electrode 28. Once positioned, and as further shown in FIG. 4C, a rotary swaging process may then be performed on the assembly to compress the ends 56,58 of the insulating sleeve 34 within the cavities 74,76. In certain embodiments, for example, a mandrel 78 is inserted into the interior of the assembly, and a number of dies are used to generate a radial compressive force F that is applied uniformly about the outer surface of the ring electrode 28. Other suitable compression techniques such as crimping can also be employed to generate the radial compressive force F about the outer surface of the ring electrode 28.

As the ring electrode 28 is compressed against the swage base 54 and insulating sleeve 34, the height of each of the cavities 74,76 decreases. In some embodiments, for example, the height of the cavities 74,76 may be reduced to approximately 75% to 100% of the thickness of the insulating sleeve 34. This reduction in the height of the cavities 74,76 further aids in establishing a mechanical bond between the insulating sleeve 34, the swage base 54, and the ring electrode 28.

Figure 4C:
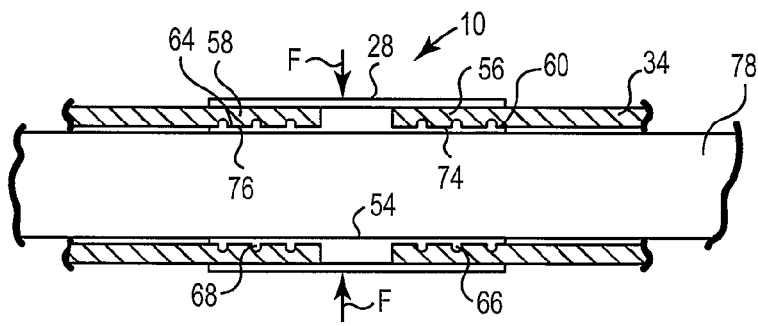
Figure 5:
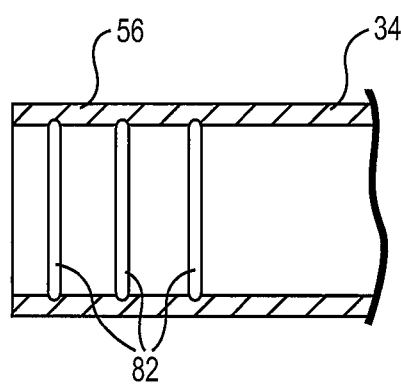
FIG. 5 is a view showing the formation of internal channels on an end of the insulating sleeve subsequent to the swaging step depicted in FIG. 4C.

As further shown in FIG. 4C, the compressive force F asserted against the ring electrode 28 during the swaging process also causes the ends 56,58 of the insulating sleeve 34 to compress within the cavities 74,76. When this occurs, the protrusions 66,68 on each of the flanges 60,64 form internal channels within the ends 56,58 of the sleeve 34. This can be seen, for example, in FIG. 5, which shows one of the ends 56 having a number of channels 82 formed within the interior of the sleeve 34 subsequent to the swaging step of FIG. 4C.

Figure 4D:
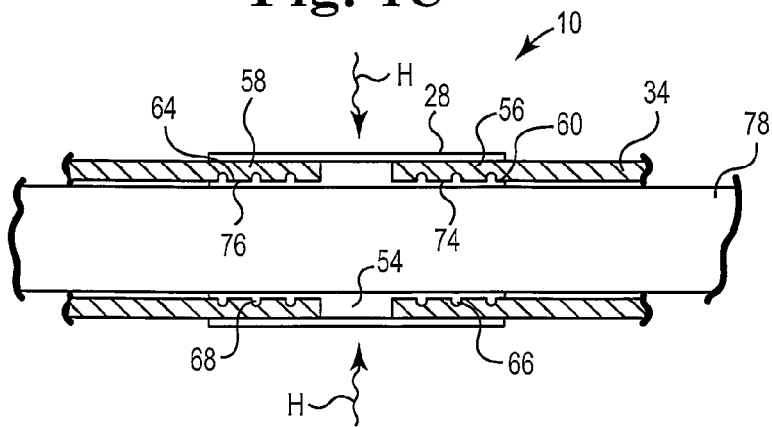

In some embodiments, and as further shown in FIG. 4D, an annealing process in which heat H is applied to the assembly can be performed to further strengthen the mechanical bond between the insulating sleeve 34 and the swage base 54 and ring electrode 28. The annealing step may be performed either during the swaging step shown in FIG. 4C, or as a separate step after swaging. In those embodiments in which the insulating sleeve 34 comprises a thermoplastic material, the annealing step may further cause the sleeve material to reflow within any voids located on the flanges 60,64 and the ring electrode 28 within the cavities 76,78, further increasing the mechanical strength of the bond. Once cured, the bonded assembly may then be subjected to additional steps to fabricate the lead.

In certain embodiments, the swaging process can be performed without the use of adhesives, forming an adhesiveless bond between the insulating sleeve 34 and the swage base 54 and electrode 28. Such an adhesiveless bond may reduce the time and cost associated with applying adhesives to the insulating sleeve 34, and may reduce cracking or fatigue caused by degradation of the adhesive material over time. In some embodiments, an adhesive material may be used in addition to the mechanical bonding provided via the swaging and annealing steps to further chemically bond the insulating sleeve 34 to the swage base 54 and ring electrode 28, if desired.

Figure 6:
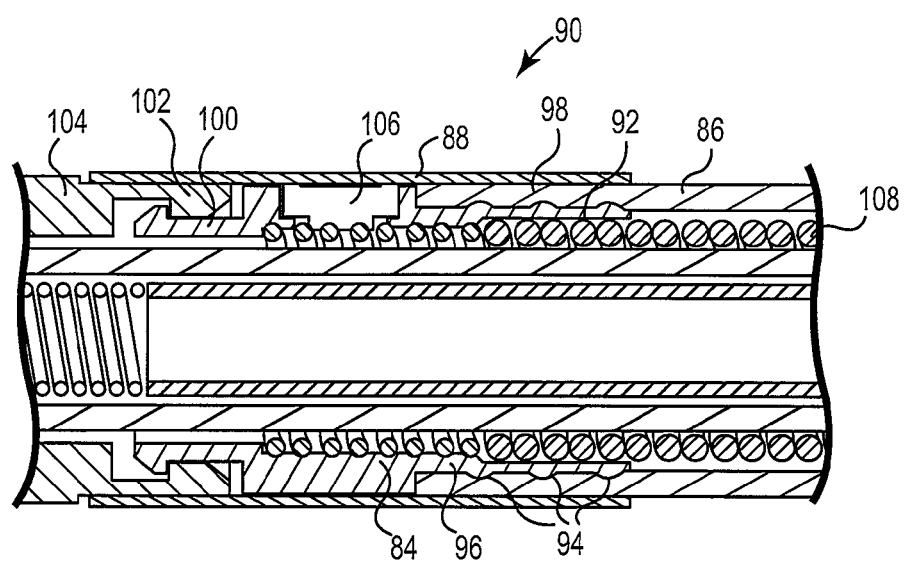
FIG. 6 is a partial longitudinal cross-sectional view showing the connection of an insulating sleeve to a swage base and ring electrode in accordance with another illustrative embodiment.

FIG. 6 is a partial, longitudinal cross-sectional view showing another illustrative swage base 84 for use in coupling an insulating sleeve 86 to a ring electrode 88 of a lead 90. In the embodiment of FIG. 6, the swage base 84 includes a proximal flange 92 having a number of protrusions 94 that extend radially outward about the circumference of an annular body 96. In certain embodiments, and as shown in FIG. 6, for example, the proximal flange 92 can include three protrusions 94 each of which engage an end 98 of the insulating sleeve 86 to form a mechanical bond between the sleeve 86 and the swage base 84 and electrode 88. The proximal flange 92 can include a greater or lesser number of protrusions depending on the engagement length between the swage base 84 and electrode 88, the thickness of the sleeve 86 at the end 98, the type of material used to form the sleeve 86, the desired mechanical characteristics of the bond between the sleeve 86 and the swage base 84 and ring electrode 88, as well as other factors.

A locking tab 100 located on a distal portion of the swage base 84 is configured to mate with and engage a corresponding tab 102 located on an adjacent component 104 of the lead 90. In certain embodiments, for example, the locking tab 100 may permit the swage base 84 to be secured to the component 104 once the insulating sleeve 86 is mechanically bonded to the swage base 84 and ring electrode 88 using a swaging and annealing process similar to that described, for example, with respect to FIGS. 4A-4D.

An access opening 106 disposed through the body 96 of the swage base 84 can be used to facilitate bonding of an internal coil conductor 108 to the base 84. In certain embodiments, for example, the opening 106 may permit access to the coil conductor 108 from a position external to the lead 90 in order to laser spot weld the conductor 108 to the body 96 of the swage base 84 during fabrication of the lead 90.

Figure 7:
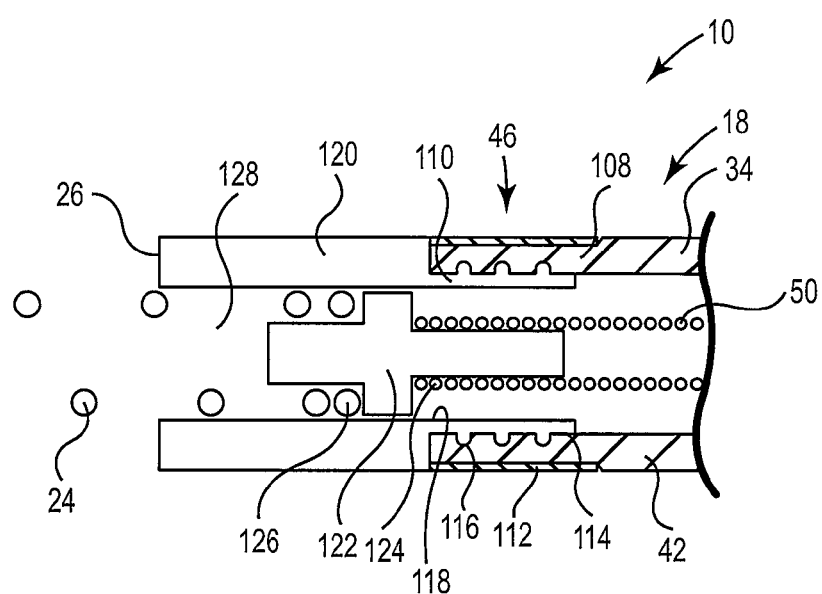
FIG. 7 is a longitudinal cross-sectional view along line 7-7 in FIG. 1 showing the connection of an insulating sleeve to the distal section of the lead.

FIG. 7 is a longitudinal cross-sectional view along line 7-7 in FIG. 1 showing the connection of the second section 42 of the insulating sleeve 34 to the lead 10. In some embodiments, and as shown in FIG. 7, an end 108 of the insulating sleeve 34 is mechanically bonded to a swage base 110 and to an annular ring 112 that radially surrounds the end 108 at joint 46. In some embodiments, the swage base 110 comprises an electrically non-conductive and rigid material such as polyetheretherketone (PEEK). In other embodiments, the swage base 110 comprises a metal, which can be electrically insulated from the surrounding vasculature via another insulating sleeve (not shown) disposed over the distal section 18 of the lead 10. The ring 112, in turn, may be formed from a rigid metal or polymeric material.

The swage base 110 includes a proximal flange 114 having a number of protrusions 116 that extend radially outward about the circumference of an annular body 118. In certain embodiments, and as shown in FIG. 7, for example, the flange 114 can include three protrusions 116 each configured to engage the end 108 of the insulating sleeve 34 during swaging to form a mechanical bond between the sleeve 34 and the swage base 110 and ring 112. The flange 114 can include a greater or lesser number of protrusions depending on the engagement length between the swage base 110 and ring 112, the thickness of the sleeve 34 at the end 108, the type of materials used in fabricating the sleeve 34, as well as other factors.

A distal, exposed portion 120 of the swage base 110 forms a rear plate at or near the distal end 26 of the lead 10, and serves to electrically insulate the interior components of the lead 10, including the second coil conductor 50, the helical tip electrode 24, and an electrode base 122. The electrode base 122 comprises an electrically conductive material such as stainless steel, platinum, MP35N, or gold, and is coupled proximally to a distal end 124 of the coil conductor 50 and distally to a proximal end 126 of the tip electrode 24. During the implantation procedure, the electrode base 122 is configured to move within an interior lumen 128 formed by the swage base 110 to permit the tip electrode 24 to be retracted out from within the distal end 26 of the lead 10.

Figure 8:
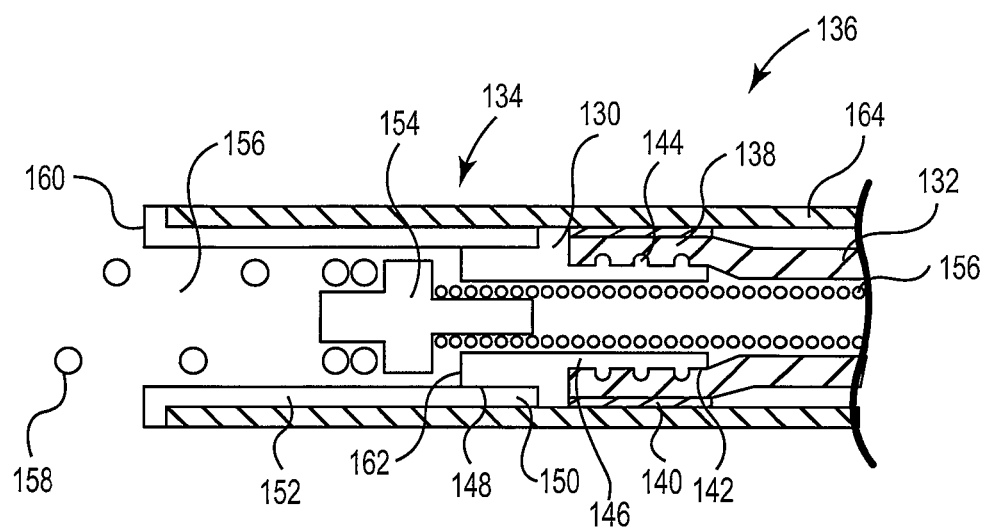
FIG. 8 is a longitudinal cross-sectional view showing the connection of an insulating sleeve to a swage base and tip electrode in accordance with another illustrative embodiment.

FIG. 8 is a partial, longitudinal cross-sectional view showing another illustrative swage base 130 for use in coupling an insulating sleeve 132 to the distal section 134 of a lead 136. In some embodiments, and as shown in FIG. 8, an end 138 of the insulating sleeve 132 is mechanically bonded to the swage base 130 and to an annular ring 140 that radially surrounds the end 138 of the sleeve 132. In some embodiments, the swage base 130 and ring 140 each comprise a rigid material such as polyetheretherketone (PEEK), stainless steel, platinum, MP35N, or gold, which facilitates swaging of the end 138 of the insulating sleeve 132 in between the swage base 130 and ring 140 during the process described herein with respect to FIGS. 4A-4D.

The swage base 130 includes a proximal flange 142 having a number of protrusions 144 that extend radially outward about the circumference of an annular body 146. In certain embodiments, and as shown in FIG. 8, for example, the proximal flange 126 can include three protrusions 144 each configured to engage the end 138 of the insulating sleeve 132 during swaging to form a mechanical bond between the sleeve 132 and the swage base 130 and ring 140. The proximal flange 142 can include a greater or lesser number of protrusions depending on the engagement length between the swage base 130 and ring 140, the thickness of the sleeve 132 at the end 138, the type of materials used in fabricating the sleeve 132, as well as other factors.

A distal shoulder 148 on the swage base 130 is configured to mate with and receive the proximal end 150 of a rigid tip housing 152. An electrode base 154 is movably received within an interior lumen 156 of the tip housing 152, and is configured to electrically connect a coil conductor 156 that extends through the lead 136 to a helical tip electrode 158 that is retracted out from within the distal end 160 of the lead 136 during the implantation procedure. A second shoulder 162 of the swage base 130, in turn, is configured to function as a proximal stop to prevent proximal movement of the electrode base 154 beyond the swage base 130. In some embodiments, an additional polymer sleeve 164 can be placed over the tip housing 152, swage base 130, and ring 140 to further insulate the lead components and to impart additional mechanical strength to the lead 136, if desired.

Figure 9:
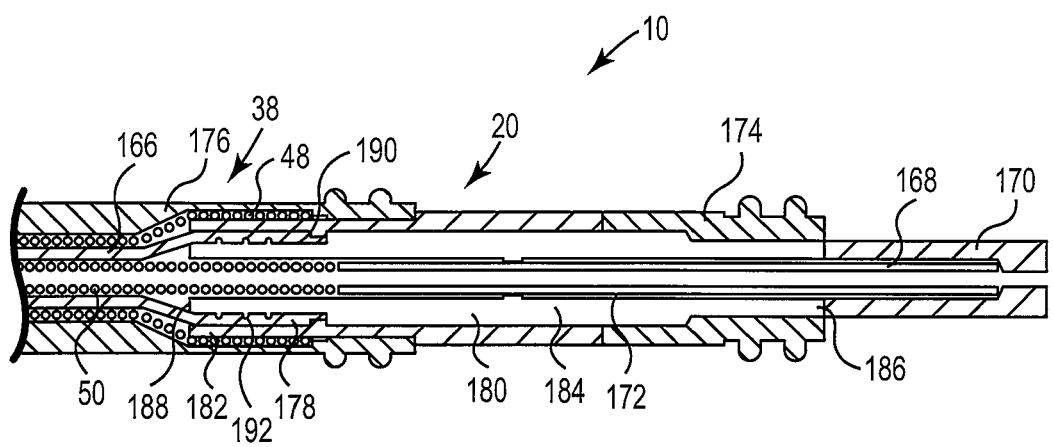
FIG. 9 is a longitudinal cross-sectional view along line 9-9 in FIG. 1 showing the connection of an insulating sleeve to the terminal connector.

FIG. 9 is a longitudinal cross-sectional view along line 9-9 in FIG. 1 showing the connection of an insulation sleeve 166 to the terminal connector 20 of the lead 10. As further shown in FIG. 9, the terminal connector 20 includes a metal terminal pin 168 and terminal pin cap 170 that electrically connect the pulse generator 12 to the first coil conductor 48 of the lead 10. The terminal connector 20 also includes a metal terminal electrode 172 that electrically connects the pulse generator 12 to the second coil conductor 50 of the lead 10. A number of seals 174,176 comprising a flexible polymeric material such as silicon or polyurethane are configured to seal the internal components of the terminal connector 20, including the terminal pin 168 and the first and second coil conductors 48,50.

The proximal end 178 of the insulating sleeve 166 is secured to a swage base 180 and to the distal end 182 of the terminal electrode 172, forming a mechanical bond at joint 38. In some embodiments, the swage base 180 includes an annular body 184 disposed radially about a portion of the terminal pin 168 and the second coil conductor 90. The annular body 184 extends from a proximal end 186 located adjacent to the terminal pin cap 170 to a distal end 188 located adjacent to the proximal end 178 of the insulating sleeve 166.

The swage base 180 includes a distal flange 190 having a number of protrusions 192 that extend radially outward about the circumference of the annular body 184 of the base 180. In certain embodiments, and as shown in FIG. 9, for example, the distal flange 190 can include three protrusions 192 each configured to engage the proximal end 178 of the insulating sleeve 166 during swaging to form a mechanical bond between the sleeve 166 and the swage base 180 and terminal electrode 172. The distal flange 190 can include a greater or lesser number of protrusions depending on the engagement length between the swage base 180 and electrode 172, the thickness of the sleeve 166 at the end 178, the type of materials used in fabricating the sleeve 166, as well as other factors.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. An implantable medical lead, comprising:
   a lead body;
   a swage base coupled to the lead body, the swage base comprising an annular body including at least one flange and one or more protrusions extending radially outward from an outer circumference of the at least one flange;
   a rigid member, the rigid member comprising an annular ring, the swage base at least partially within the annular ring;
   a polymeric member interposed at least in part between the outer circumference of the at least one flange and the rigid member, the polymeric member comprising a flexible tubular member that extends distally or proximally beyond the swage base and the rigid member to define an exterior surface of the lead body, the annular ring radially surrounding at least part of the flexible tubular member, the at least one flange at least partially within the flexible tubular member; and
   a compression joint mechanically bonding the polymer member to the swage base and the rigid member, wherein a portion of the flexible tubular member is in contact with, and compressed between, the one or more protrusions and the rigid member.

2. The implantable medical lead of claim 1, wherein the annular ring is a ring electrode.

3. The implantable medical lead of claim 2, wherein the lead further includes a terminal connector, and wherein the ring electrode is a terminal electrode.

4. The implantable medical lead of claim 2, wherein the swage base comprises an electrically conductive material.

5. The implantable medical lead of claim 4, wherein the swage base electrically connects the ring electrode to a coil conductor.

6. The implantable medical lead of claim 1, wherein the flexible tubular member is a sleeve.

7. The implantable medical lead of claim 1, wherein an inner surface of the annular ring is in contact with an outer surface of the portion of the flexible tubular member and an inner surface of the portion of the flexible tubular member is in contact with an outer surface of the swage base.

8. The implantable medical lead of claim 1, wherein each of the protrusions extend radially outward about a circumference of the annular body.

9. The implantable medical lead of claim 1, wherein the at least one flange comprises a first flange and a second flange, and wherein the one or more protrusions for at least one of the first or second flanges includes a plurality of protrusions extending radially outward from the outer circumference.

10. The implantable medical lead of claim 1, wherein the swage base further includes a locking tab.

11. The implantable medical lead of claim 1, wherein the polymeric member comprises an insulating sleeve.

12. An implantable medical lead, comprising:
    a coil conductor electrically coupled to an electrode;
    a metal swage base coupled to the coil conductor and electrode, the swage base comprising an annular body including at least one flange and a plurality of bumps extending radially outward from an outer circumference of the at least one flange;
    at least one polymer sleeve interposed at least in part between the outer circumference of the at least one flange and the electrode, the electrode radially surrounding at least part of each of the swage base and the at least one polymer sleeve, the polymer sleeve including a number of channels each in compression with a corresponding bump of the swage base, the polymer sleeve extending distally or proximally beyond the swage base and the electrode to define an exterior surface of the implantable medical lead; and
    a compression joint mechanically bonding the polymer sleeve to the swage base and the electrode, wherein a portion of the polymer sleeve is compressed between the plurality of bumps and the electrode.

13. The implantable medical lead of claim 12, wherein the electrode is a ring electrode.

14. The implantable medical lead of claim 12, wherein the lead further includes a terminal connector, and wherein the electrode is a terminal electrode.

15. The implantable medical lead of claim 12, wherein each of the bumps extend radially outward about a circumference of the annular body.

16. The implantable medical lead of claim 12, wherein the at least one flange comprises a proximal flange and a distal flange and the at least one polymer sleeve comprises a first polymer sleeve and a second polymer sleeve, wherein the one or more protrusions for the proximal flange includes a plurality of bumps configured to engage an end of a first polymeric sleeve, and wherein the one or more protrusions for the distal flange includes a plurality of bumps configured to engage an end of a second polymeric sleeve.

17. An implantable medical lead, comprising:
a lead body;
a swage base coupled to the lead body, the swage base comprising an annular body;
a rigid member;
a polymer sleeve interposed at least in part between the outer circumference of the at least one flange and the rigid member, the rigid member radially surrounding at least part of each of the swage base and the polymer sleeve, the polymer sleeve extending distally or proximally beyond the swage base and the rigid member to define an exterior surface of the lead body; and
a compression joint mechanically connecting the swage base to the rigid member, the polymer sleeve compressed between the swage base and the rigid member.

18. The implantable lead of claim 17, wherein the swage base comprises an annular body including one or more protrusions extending radially outward from an outer circumference of the annular body.

19. The implantable lead of claim 18, wherein the one or more protrusions impart localized compressive stresses to an interior wall of the polymer sleeve.

20. The implantable lead of claim 18, wherein the one or more protrusions impart one or more semi-circular channels within the polymer sleeve.

* * * * *